(12) United States Patent
Syn

(10) Patent No.: US 12,004,983 B2
(45) Date of Patent: Jun. 11, 2024

(54) GASTRIC REDUCTION APPARATUS AND RELATED METHODS

(71) Applicant: Syn LLC, Lubbock, TX (US)

(72) Inventor: David Syn, Lubbock, TX (US)

(73) Assignee: Syn LLC, Lubbock, TX (US)

( * ) Notice: Subject to any disclaimer, the term of this patent is extended or adjusted under 35 U.S.C. 154(b) by 0 days.

(21) Appl. No.: 18/338,433

(22) Filed: Jun. 21, 2023

(65) Prior Publication Data

US 2023/0329889 A1 Oct. 19, 2023

Related U.S. Application Data

(62) Division of application No. 16/413,143, filed on May 15, 2019, now Pat. No. 11,684,503.

(51) Int. Cl.
*A61F 5/00* (2006.01)
*A61B 17/00* (2006.01)

(52) U.S. Cl.
CPC ...... *A61F 5/0089* (2013.01); *A61B 17/00234* (2013.01); *A61F 5/0076* (2013.01); *A61B 2017/00557* (2013.01); *A61B 2017/00566* (2013.01); *A61B 2017/00818* (2013.01)

(58) Field of Classification Search
CPC .... A61M 2025/1043; A61M 2025/105; A61M 2025/1086; A61F 5/0076; A61F 5/0083; A61F 5/0089; A61B 17/00234; A61B 2017/00557; A61B 2017/00566; A61B 2017/00818; A61B 2017/306
See application file for complete search history.

(56) References Cited

U.S. PATENT DOCUMENTS

| | | | | |
|---|---|---|---|---|
| 4,693,243 A * | 9/1987 | Buras | ............... | A61M 16/0486 604/103.01 |
| 5,049,132 A * | 9/1991 | Shaffer | ............. | A61M 16/0456 604/101.02 |
| 5,146,916 A * | 9/1992 | Catalani | ............... | A61M 16/04 128/207.14 |
| 5,213,576 A * | 5/1993 | Abiuso | ............. | A61M 16/0456 604/101.02 |
| 5,409,012 A * | 4/1995 | Sahatjian | ........... | A61B 10/0275 600/562 |
| 5,611,775 A * | 3/1997 | Machold | ............ | A61M 25/1011 604/509 |
| 5,693,029 A * | 12/1997 | Leonhardt | ............. | A61M 29/02 604/523 |
| 6,398,757 B1 * | 6/2002 | Varenne | ................. | A61K 38/44 604/103.02 |
| 7,335,210 B2 * | 2/2008 | Smit | ..................... | A61F 5/0076 606/108 |
| 7,779,845 B2 * | 8/2010 | Ortiz | ................. | A61B 17/0218 128/898 |
| 9,179,921 B1 * | 11/2015 | Morris | ............ | A61B 17/12136 |
| 9,439,633 B2 * | 9/2016 | O'Dea | ............ | A61M 25/10181 |

(Continued)

*Primary Examiner* — Ryan J. Severson
(74) *Attorney, Agent, or Firm* — Carder W. Brooks

(57) ABSTRACT

The invention relates to a method and apparatus for endoscopically shaping and standardizing the size of a sleeved stomach for use in gastric reduction surgery. The device and method standardize and streamline gastric reduction surgery, specifically vertical sleeve gastrectomy, providing a guide for creating the stomach reduction and also shaping a stomach which will maintain an appropriate structure post-surgery.

20 Claims, 5 Drawing Sheets

(56) References Cited

U.S. PATENT DOCUMENTS

| | | | | |
|---|---|---|---|---|
| 9,517,073 B1* | 12/2016 | Morris | | A61B 17/12045 |
| 9,700,661 B2* | 7/2017 | Gerber | | B01D 65/02 |
| 9,724,096 B2* | 8/2017 | Thompson | | A61B 17/07207 |
| 9,987,157 B1* | 6/2018 | McCarty | | A61B 17/29 |
| 9,999,533 B2* | 6/2018 | Radl | | A61B 17/07207 |
| 10,470,911 B2* | 11/2019 | Thompson | | A61B 90/06 |
| 10,610,663 B2* | 4/2020 | Rajagopalan | | A61B 5/4255 |
| 11,684,503 B2* | 6/2023 | Syn | | A61F 5/0089 |
| | | | | 600/37 |
| 2002/0013601 A1* | 1/2002 | Nobles | | A61M 29/02 |
| | | | | 606/193 |
| 2003/0191476 A1* | 10/2003 | Smit | | A61F 5/0076 |
| | | | | 606/108 |
| 2004/0153116 A1* | 8/2004 | Nobles | | A61B 1/32 |
| | | | | 606/193 |
| 2005/0149072 A1* | 7/2005 | DeVries | | A61B 17/0469 |
| | | | | 606/153 |
| 2007/0032702 A1* | 2/2007 | Ortiz | | A61B 17/2812 |
| | | | | 600/205 |
| 2007/0191766 A1* | 8/2007 | McMorrow | | A61M 25/1002 |
| | | | | 604/103.01 |
| 2007/0225744 A1* | 9/2007 | Nobles | | A61M 29/02 |
| | | | | 606/192 |
| 2011/0118650 A1* | 5/2011 | Nihalani | | A61F 5/0079 |
| | | | | 604/9 |
| 2012/0277525 A1* | 11/2012 | O'Dea | | A61B 5/0538 |
| | | | | 604/8 |
| 2012/0277552 A1* | 11/2012 | Gerber | | A61B 5/0537 |
| | | | | 604/503 |
| 2014/0081176 A1* | 3/2014 | Hassan | | A61B 90/06 |
| | | | | 600/593 |
| 2014/0148731 A1* | 5/2014 | Radl | | A61F 5/0089 |
| | | | | 600/593 |
| 2016/0015385 A1* | 1/2016 | Kawaura | | A61B 17/062 |
| | | | | 600/30 |
| 2016/0015387 A1* | 1/2016 | Kawaura | | A61B 17/06109 |
| | | | | 606/185 |
| 2016/0067074 A1* | 3/2016 | Thompson | | A61F 5/0086 |
| | | | | 606/153 |
| 2017/0112651 A1* | 4/2017 | Sasse | | A61B 5/4238 |
| 2017/0172571 A1* | 6/2017 | Thompson | | A61B 17/07207 |
| 2018/0193590 A1* | 7/2018 | Rajagopalan | | A61B 5/6885 |
| 2020/0360168 A1* | 11/2020 | Syn | | A61F 5/0089 |
| 2021/0162185 A1* | 6/2021 | Smith | | A61M 25/10 |
| 2023/0329889 A1* | 10/2023 | Syn | | A61F 5/0083 |

* cited by examiner

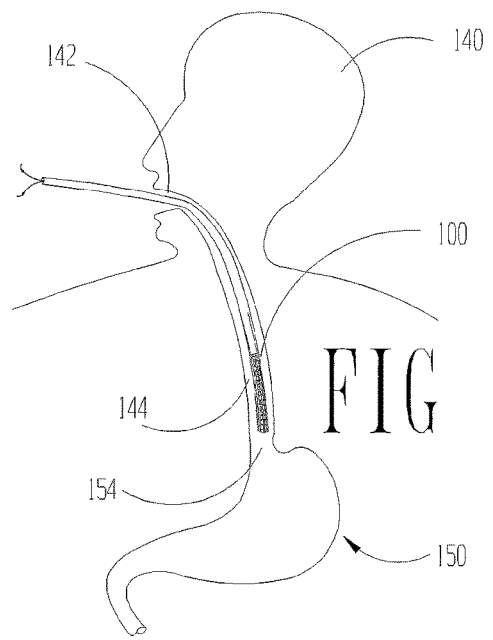
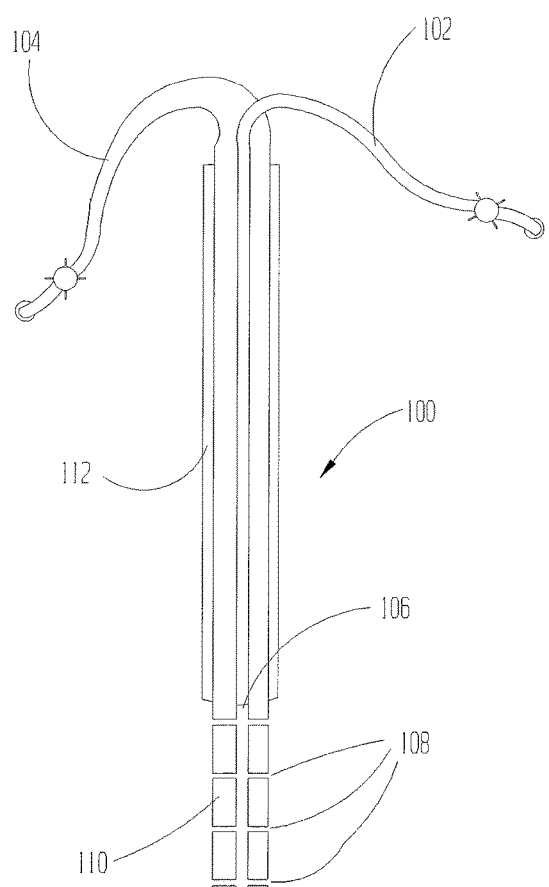
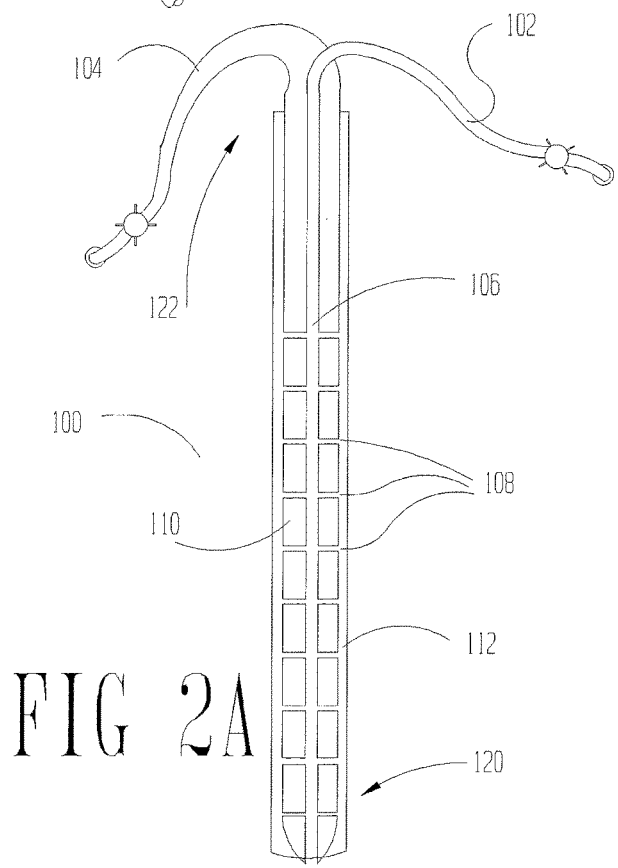

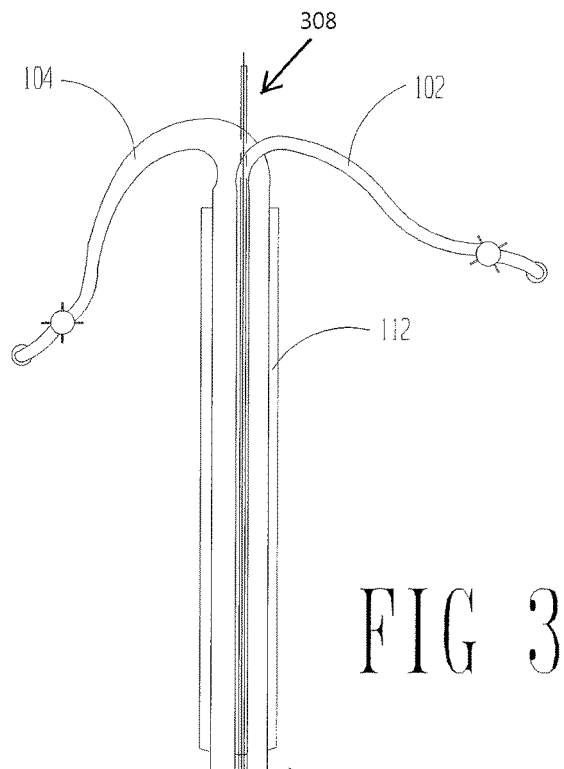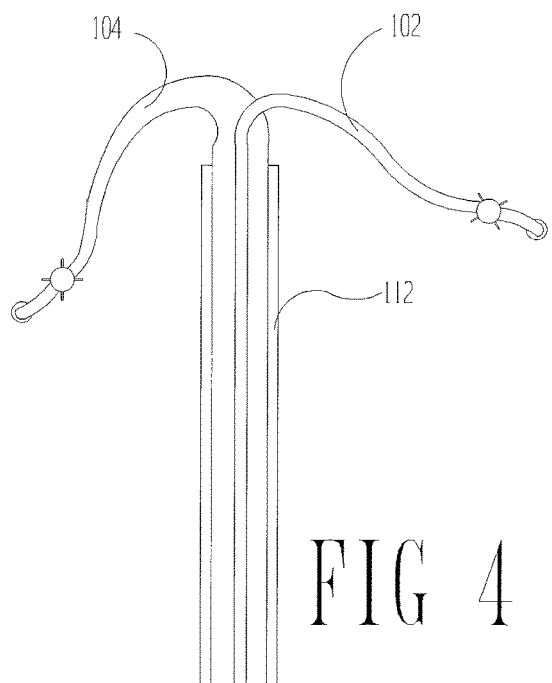

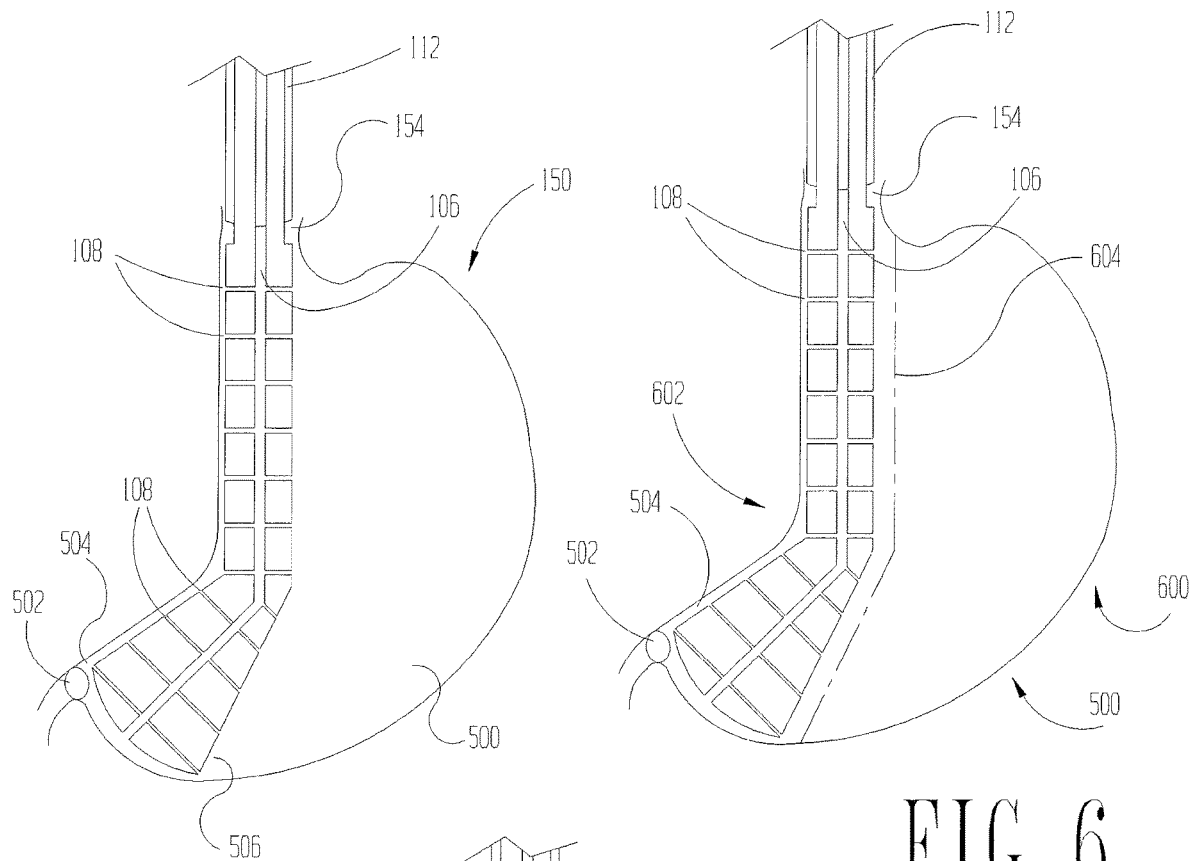
FIG 5
FIG 6
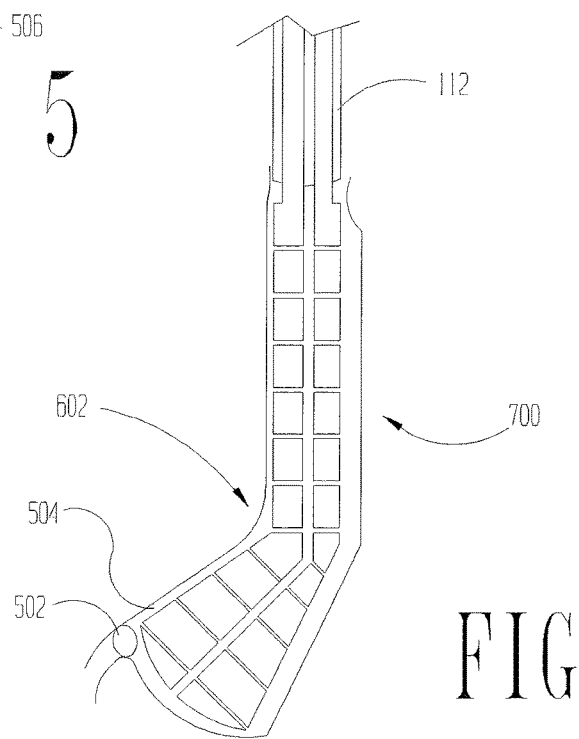
FIG 7

GASTRIC REDUCTION APPARATUS AND RELATED METHODS

CROSS-REFERENCE TO RELATED APPLICATIONS

Any and all applications for which a foreign or domestic priority claim is identified in the Application Data Sheet (either filed with the present application or subsequently amended) are hereby incorporated by reference under 37 CFR § 1.57. This application is a divisional application of, and cross references, U.S. patent application Ser. No. 16/413,143, "Gastric Reduction Apparatus and Related Methods," filed on May 15, 2019, which is herein incorporated by reference as an example.

STATEMENT OF FEDERALLY SPONSORED RESEARCH OR DEVELOPMENT

None.

REFERENCE TO A SEQUENCE LISTING, A TABLE, OR A COMPUTER LISTING COMPACT DISC APPENDIX

None.

BACKGROUND OF THE INVENTION

The present invention relates to gastric reduction surgery, specifically vertical sleeve gastrectomy. The invention relates to a method and apparatus for endoscopically shaping and standardizing the size of a sleeved stomach.

Morbid obesity is a serious medical condition increasing in incidence in the United States and world-wide. Morbid obesity with and without its comorbidities markedly decreases life expectancy. Surgical treatment for morbid obesity has proven to be the only effective and durable method of treatment and is far superior to medical interventions.

Many surgical interventions have been developed to treat morbid obesity and its comorbidities. The field of bariatric and metabolic surgery has evolved and continues to evolve as some surgical treatments have been found to be less effective than others. Some of the older methods that have become less popular include the Vertical Banded Gastroplasty, Non-adjustable gastric band and the adjustable LapBand. The more effective and more commonly performed surgeries today include the Vertical Sleeve Gastrectomy, Roux-en-Y Gastric Bypass and Biliopancreatic Diversion with a Duodenal Switch. In 2017 approximately 228,000 bariatric surgeries were performed in the United States alone. Of those surgeries, more than 59% were the Vertical Sleeve Gastrectomy. It is estimated that an additional 3.5% of the surgeries performed also have a sleeved stomach as part of the surgery as is the case with the Biliopancreatic Diversion with a Duodenal Switch. The Vertical Sleeve Gastrectomy has overtaken the Roux-en-Y Gastric Bypass as the most commonly performed bariatric surgery worldwide.

The Vertical Sleeve Gastrectomy involves removing approximately 70% of the stomach along the greater curvature, resulting in a relatively tubular shaped upper stomach with preservation of the antrum. This is accomplished via stapling the stomach in a relatively straight fashion starting from the antrum and heading to angle of His and then removing the sleeve gastrectomy specimen which would include the majority of the body and fundus of the stomach. There is no bypassing of intestine in the standard Vertical Sleeve Gastrectomy.

Sleeving the stomach may sound to be a relatively simple matter, however if done incorrectly, can result in serious complications such as stricture resulting in intractable nausea and vomiting and reflux, twisting of the staple line which can result in folding of the sleeved stomach upon itself, misaligned staple lines which can result in catastrophic leaks. Surprisingly and unfortunately, even though the Vertical Sleeve Gastrectomy has become the most commonly performed bariatric operation in the world, the manner in which a stomach is sleeved is not standardized. Bougie sizes used to shape the sleeve range from 32 to 40 French. Some surgeons use devices utilizing suction and some not and the amount of antrum preserved is highly variable. It is basically dealers' choice with no standardization.

Experienced surgeons proficient in performing Vertical Sleeve Gastrectomy however agree upon certain key points when creating a sleeve stomach. Relatively larger bougie sizes should be utilized in order to prevent stricture. Care should be taken to keep the upper portion of the sleeved stomach as straight and tubular as possible with equal amounts of stomach preserved anteriorly and posteriorly in order to prevent twisting of the staple line and stricturing. The majority of the antrum should be preserved to prevent dysphagia.

This is a problem that has not been successfully solved by current devices or methods. Devices such as McCarty (U.S. Pat. No. 9,987,157) are not standardized to maintain the needed portions of the patient's stomach, such as the antrum, by temporarily attaching to the inner walls of the stomach as in the claimed invention. Additionally, other devices and methods still require a separate guide mechanism as in Thompson et al. (U.S. Ser. No. 14/846,764) and Thompson et al. (U.S. Pat. No. 9,724,096). The claimed invention solves these problems by integrating, in a single device and streamlined method, an attachment method to preserve critical portions of the stomach while also providing a guide to for performing a gastrectomy.

Because of the serious complications that can result from misshaped sleeves, it is desirable to provide instruments and methods that will help to position and orient the stomach in order to create a standardized shape and size for a properly formed consistently shaped sleeved stomach. The present invention provides an instrument and method for assisting in the performance of a standardized Vertical Sleeve Gastrectomy resulting in reduced patient morbidity.

SUMMARY OF THE INVENTION

The object of the present invention is to provide an inflatable, articulating, adjustable endoscopic instrument for properly shaping the stomach in order to standardize the shape and preserve the antrum of the stomach as well as prevent stricture and prevent twisting of the staple line during stapling of the stomach while creating a Vertical Sleeve Gastrectomy. Intra-operative measurements of 500 decompressed stomachs where made in order to ascertain the average dimensions from the gastroesophageal junction to the angularis incisura, the angularis incisura to the antrum on the greater curvature, and from the angularis incisura to the pylorus.

In one embodiment the claimed invention is a method of treating a patient, comprising the steps of inserting a gastric reduction surgery assistance apparatus through the patient's mouth and into their esophageal tract; deploying a balloon from a cylindrical outer sheath of the gastric reduction surgery assistance apparatus to extend into the patient's stomach; inflating the balloon within the patient's stomach; engaging the plurality of hollow channels of the balloon to seal against the patient's stomach's inner walls; excising the excess stomach and closing the patient's stomach; removing the gastric reduction surgery assistance apparatus.

In one embodiment, the deploying step may comprise deploying a balloon from the distal end of the cylindrical outer sheath of the gastric reduction surgery assistance apparatus into the patient's stomach. In another embodiment, the cylindrical outer sheath may be inserted into the patient's stomach. In this embodiment, the balloon may be deployed by retracting the cylindrical outer sheath, exposing the balloon. The balloon may be comprised of an inflatable material such as rubber, latex, polychloroprene, or nylon. In one embodiment, the inflating step may comprise inflating the balloon with a gas or a liquid to between 35 and 45 French at the proximal 8 to 12 centimeters of the balloon. The gas may be any gas such as oxygen or nitrogen. The liquid may be any fluid liquid such as water or saline. Further, the inflating step may further comprise inflating a balloon cylindrical member having a length of 13 to 17 centimeters and wherein the distal 3 to 7 centimeters of the balloon cylindrical member angles from to between 130 and 140 degrees aligning with the lesser curvature of the stomach and extending into the antrum of the stomach. In one embodiment, the angle may be inherent in the balloon shape and angle on inflation. In another embodiment, the balloon may be inflated and then manually angled to fit against the lesser curvature of the patient's stomach. In either angling embodiment, the balloon angle may be tailored to fit against a plurality of sizes of patient stomach's and lesser curvatures.

In one embodiment, the inflating step further comprises inflating the remaining distal 3 to 7 centimeters of the balloon into a bell shape with the proximal end inflated to 35 to 45 French and the distal end inflated to 145 to 155 French.

In one embodiment, the engaging step comprises engaging the plurality of hollow channels wherein a negative pressure is applied through the hollow channels, sealing the balloon against the lesser curvature lateral, anterior, and posterior internal walls of the patient's stomach. In a preferred embodiment, the hollow channels will engage the lateral lesser curvature side, the anterior side, and the posterior side of the patient's stomach. By engaging the three sides of the patient's stomach and pulling the anterior side and posterior side together, a new greater curvature of the stomach may be formed.

In one embodiment, the excising step comprises removing the excess greater curvature lateral stomach not sealed to the balloon and sealing the patient's stomach together around the balloon. The excising may be performed by cutting with a sharp utensil such as a laparoscopic knife. The sealing may be performed by stapling or suturing with tools such as a surgical stapling device. In a preferred embodiment, the balloon edge may be used as a guide for cutting. By doing so, there is less room for user error in the excision step and the excision may be standardized. In one embodiment, the greater curvature lateral edge of the balloon may have further guide assistance. In one embodiment, this guidance may be illumination such as light emitting diodes (LEDs) placed on the balloon to guide a surgeon in excising the stomach along the edge of the balloon. In another embodiment, this guidance may be a rough edge or texture of the balloon to guide a surgeon in excising the stomach along the edge of the balloon.

In a preferred embodiment, the removing step comprises disengaging the suction of the plurality of hollow channels then deflating the balloon thereby unsealing the balloon from the internal lining of the patient's stomach. The new shape of the stomach is maintained after deflating the balloon and a new greater curvature now exists. The removing step further comprises removing the gastric reduction surgery assistance apparatus and deflated balloon through the patient's esophageal tract and out through the patient's mouth.

In one embodiment, the claimed invention is a gastric reduction surgery assistance apparatus comprising an outer sheath inserted into the patient's esophageal tract; an inflatable and deflatable balloon cylindrical member capable of being deployed and retracted from said outer sheath comprising hollow channels opening on the exterior surface of the balloon and converging to one channel within the balloon. In one embodiment, the length of the balloon cylindrical member is between 13 and 17 centimeters. In one embodiment, the distal 3 to 7 centimeters of the member is angled when inflated to between 130 and 140 degrees aligning with the antrum of the patient's stomach.

In one embodiment, the balloon is inflated and deflated by an inflation tube running from the balloon cylindrical member through the outer sheath and out of the patient where inflation and deflation are controlled by an inflation pump. In one embodiment, the proximal 8 to 12 centimeters of balloon is between 35 and 45 French when inflated with the remaining 3 to 7 centimeter distal end of the balloon inflated to a bell shape of 35 to 45 French at its proximal end and 145 to 155 French at its distal end. The balloon is inflated by an inflation pump using a gas or a liquid.

In one embodiment, the balloon comprises a plurality of hollow channels opening on the exterior of the balloon and converging to one channel within the outer sheath with that one channel continuing as a hollow tube running through the outer sheath and out of the patient where a negative pressure may be applied and controlled by a suction pump. By converging to one channel within the balloon, pressure applied to this one channel will then be extended to the plurality of channels opening on the outer edge of the balloon. In a preferred embodiment, the hollow channels increase in diameter as the balloon inflates, facilitating more efficient pressure transfer. In a preferred embodiment, the balloon is inflated when pressure is applied to the channel within the balloon, thereby better facilitating pressure transfer to the plurality of hollow channels because they will be supported by the balloon's inflation.

In a preferred embodiment, the method of performing gastric reduction surgery using an assistance device as claimed can be used to standardize gastric reduction surgery. By standardizing the method of performing the surgery, the surgery can be performed with fewer errors or complications, thereby increasing surgery success rates and increasing patient quality of life.

BRIEF DESCRIPTION OF THE DRAWINGS

These and other features, aspects, and advantages of the present invention will become better understood with regard to the following descriptions, appended claims, and accompanying drawings where:

FIG. 1 shows the insertion of the device through the patient's mouth.

FIG. 2A shows the device in an uninflated state.

FIG. 2B illustrates the balloon protruding from the outer sheath.

FIG. 3 shows the device as it continues to inflate and details the inner channels of the balloon.

FIG. 4 depicts the balloon as it continues to inflate.

FIG. 5 shows the fully inflated balloon within the patient's stomach.

FIG. 6 shows the fully inflated device within the patient's stomach.

FIG. 7 shows the removal of the greater curvature of the patient's stomach while the device continues to be fully inflated within the patient's stomach.

DETAILED DESCRIPTION OF THE INVENTION

Figure 2C:
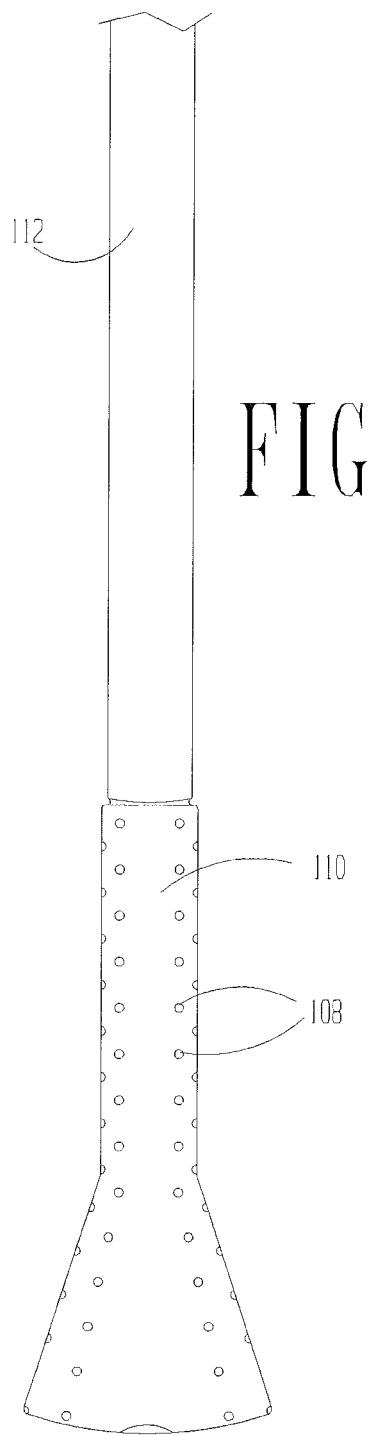
FIG. 2C depicts the inflated balloon with a plurality of hollow channels opening on the outer edge of the balloon.
Figure 2D:
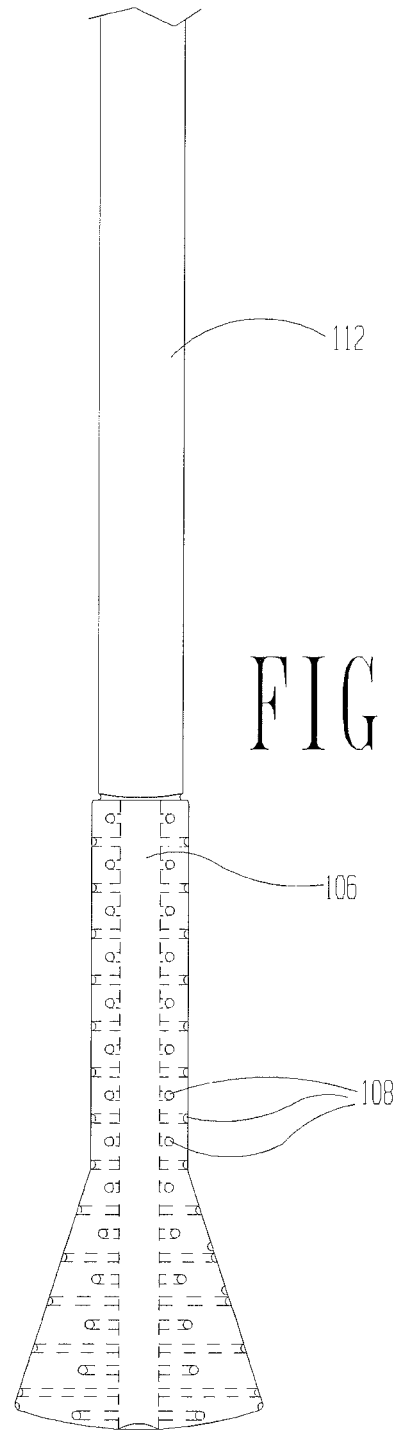
FIG. 2D depicts the network of hollow channels converging to a central hollow channel in the balloon.

In the Summary of the Invention above and in the Detailed Description of the Invention, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference if made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

As shown in FIGS. 1, 2A, and 2B, one embodiment of the claimed gastric reduction surgery assistance apparatus and methods applied to a patient 140 comprises an insertion tube 100 that is inserted into the patient's mouth 142 and into their esophageal tract 144. In a preferred embodiment, the insertion tube 100 comprises a cylindrical outer sheath 112. The cylindrical outer sheath 112 is comprised of rigid or semi-rigid material that is non-toxic. Contained in the cylindrical outer sheath 112 is a balloon 110 in a deflated state. In a preferred embodiment, the balloon 110 is comprised of a collapsible material such as rubber or latex, capable of maintaining a rigid structure when inflated.

As depicted in FIGS. 1, 2A, and 2B, in a preferred embodiment, the cylindrical outer sheath 112 is inserted down the patient's esophageal tract 144 until the distal end of the cylindrical outer sheath 112 reaches through the patient's esophageal sphincter 154. In a preferred embodiment, at least one inflation controlling channel 104 of the balloon 110 will extend from the proximal end of the cylindrical outer sheath 122, through the patient's esophageal tract 144, and out of the patient's mouth 142. The channel can be sealed to and controlled by an inflation pump outside of the patient's mouth 142. In one embodiment, the pump can pump gas or liquid to fill the balloon 110 within the patient's stomach 150. In a preferred embodiment, the cylindrical outer sheath 112 slides up, exposing the balloon 110. The cylindrical outer sheath 112 may be slid up by mechanical means such as an attached line running to outside of the patient, or by the force of the balloon 110 inflating.

In a preferred embodiment, at least one suction controlling channel 102 will extend from the proximal end of the cylindrical outer sheath 122, through the patient's esophageal tract 144, and out of the patient's mouth 142. The suction controlling channel can be sealed to a suction pump or negative pressure pump outside of the patient's mouth 142. In a preferred embodiment, the suction pump or negative pressure pump will apply negative pressure through the suction controlling channel 102 and to the plurality of hollow channels that open on the outer edges of the balloon 108 in the patient's stomach 150.

As shown in FIGS. 2A, 2B, 2C, 2D, and 3, in one embodiment, the balloon 110 comprises a plurality of hollow channels that open on the outer edges of the balloon 108 and converge to one channel within the balloon 106. In one embodiment, the converged channel 106 is connected to a suction controlling channel 102 outside of the patient's body that can be engaged once the balloon 110 is inflated. In one embodiment, the hollow channel openings 108 are circular in shape allowing temporary suction attachment to a patient's interior stomach wall. In another embodiment, the hollow channel openings 108 may be another shape, allowing tailored temporary suction attachment to a patient's interior stomach wall. In one embodiment, the hollow channel openings 108 may be uniformly spaced and patterned on the outer edges of the balloon. In another embodiment, the hollow channel openings 108 may be scattered randomly over the outer edges of the balloon to allow better temporary suction attachment to a plurality of stomach shapes. In yet another embodiment, the hollow channel openings 108 may be spaced over the outer edges of the balloon such to optimize specific temporary suction attachment to a plurality of stomach shapes.

In a preferred embodiment, the plurality of hollow channel openings 108 are grouped on the outer surface of the balloon 110 to primarily apply suction and temporarily attach to the posterior, anterior, and lateral lesser curvature of the patient's stomach. In one embodiment, to accomplish this, hollow channel openings 108 are only present on the posterior, anterior, and lateral left curvature outer edges of the balloon 108. In another embodiment, larger diameter hollow channel openings 108 are present on the posterior, anterior, and lateral left curvature outer edges of the balloon 108 while smaller diameter hollow channel openings 108 are present on the lateral greater curvature outer edge of the balloon 108, thereby facilitating a stronger temporary connection to the posterior, anterior, and lateral lesser curvature outer edges of the balloon 108 and a weaker temporary connection to the lateral greater curvature outer edge of the balloon 108.

As shown in FIGS. 2B, 2C, 2D, and 3, in one embodiment, when the inflation pump is engaged and the balloon 110 is inflated, the balloon 110 extends out of the cylindrical outer sheath 112, through the patient's esophageal sphincter 154, and into the patient's stomach 150. In another embodiment, the distal end of the cylindrical outer sheath 120 extends through the esophageal sphincter 154 and allows the balloon to only extend out into the patient's stomach 150. In a preferred embodiment, the cylindrical outer sheath 112 is slid up the suction controlling channel 102 and the inflation controlling channel 104 to expose the balloon 110 within the patient's stomach 150. The balloon 110 extends out of the cylindrical outer sheath 112 and maintains a cylindrical shape. In one embodiment, the proximal end of the inflated balloon 304 is between 8 and 12 centimeters in length and 35 and 45 French in width. In a preferred embodiment, the proximal end of the inflated balloon 304 is 10 centimeters in length and 40 French in width.

As further depicted in FIG. 3, as the balloon is inflated, the distal end of the inflated balloon 306 forms a shape that angles to between 130 and 140 degrees 300 on the inner angle. In a preferred embodiment, the angle of bend is 135 degrees 300. In one embodiment, the distal end of the inflated balloon 306 is between 3 and 7 centimeters in length. In a preferred embodiment, the distal end of the inflated balloon 306 is 5 centimeters in length.

Specifically shown in FIG. 3, in one embodiment, an angling assistance device 308 may be inserted down and through the converged channel 106. In one embodiment, the angling assistance device 308 may be a thin rigid structure, such as a wire, that is angled to manipulate the distal end of the inflated balloon 306.

As shown in FIG. 4, as the balloon 110 continues to inflate, in one embodiment, the final inflated form of the distal end of the inflated balloon 306 forms a bell shape 400. In one embodiment, the proximal end of the bell shape 402 is between 35 and 45 French in width. In one embodiment, the distal end of the bell shape 404 is between 145 and 155 French in width. In a preferred embodiment, the proximal end of the bell shape 402 is 40 French in width and the proximal end of the bell shape 404 is 150 French in width. FIG. 5 shows one embodiment of the fully inflated balloon 110 within the patient's stomach 150.

As shown in FIG. 5, the bell shape 400 of the inflated balloon 110 follows the lesser curvature lateral side of the patient's stomach 150 and extends into the stomach's antrum 506. In one embodiment, the bell shape 400 of the inflated balloon 110 stops at the stomach's antrum 506 and does not extend past into the patient's pyloric canal 504 or pyloric sphincter 502. In another embodiment, the bell shape 400 of the inflated balloon 110 may extend further into the patient's pyloric canal 504 or to the pyloric sphincter 502, depending on patient stomach size.

As shown in FIG. 6, once the balloon 110 is fully inflated within the patient's stomach 150, the suction controlling channel within the balloon 106 can be engaged. Once engaged, the suction controlling channel within the balloon 106 applies negative pressure to the plurality of hollow channel openings 108 on the outer edges of the balloon. In one embodiment, this negative pressure temporarily affixes the inflated balloon 110 to the lesser curvature 602 of the patient's stomach 150. In a preferred embodiment, the inflated balloon 110 is temporarily affixed to the lateral lesser curvature 602, anterior, and posterior walls of the patient's stomach 150.

As shown in FIG. 6, once the suction controlling channel within the balloon 106 applies negative pressure to the plurality of hollow channel openings 108 on the outer edges of the inflated balloon, in one embodiment, the greater curvature 600 of the patient's stomach 150 is left loose and unaffixed to the balloon 110. In a preferred embodiment, the greater curvature 600 of the patient's stomach 150 may then be excised from the rest of the stomach, thereby performing a gastric reduction. Excision may be performed by any standard method in the gastric reduction practice, including but not limited to stapling along lateral edge formed by the balloon 110 and then cutting the excess greater curvature 600 with laparoscopic knife, thereby forming a new greater curvature 700. In a preferred embodiment, the lateral greater curvature is used as a guide for stapling the patient's stomach 150 to create a new greater curvature 700 along the edge of the balloon 110, and thereby standardizing the gastrectomy procedure.

As shown in FIGS. 6 and 7, in a preferred embodiment, the greater curvature 600 of the patient's stomach 150 is excised by cutting the stomach along the inflated balloon 604. In a preferred embodiment, once the greater curvature 600 of the patient's stomach 150 is excised, the anterior and posterior portions of the remaining stomach may be sealed together along the edge of the inflated balloon 604, thereby completing a gastric reduction in size to the patient's stomach 150. The sealing of the anterior edge of the stomach to the posterior edge of the stomach forms a new, smaller greater curvature 700. The sealing may be performed by any standard method in the gastric reduction practice, including but not limited to stapling or suturing.

In one embodiment, by sealing the smaller greater curvature along the edge of the inflated balloon 604, standardization of the gastric reduction surgery can be achieved in which the stomach's antrum 506 is preserved. In a preferred embodiment, the edge of the inflated balloon 604 acts as a guide to the surgeon, allowing for a uniform method of sealing and performing gastric reduction surgery by creating a smaller greater curvature 700 of the patient's stomach.

Once the sealing has been completed and the smaller greater curvature 700 has been formed, in a preferred embodiment, the apparatus may be removed.

Figure 8:
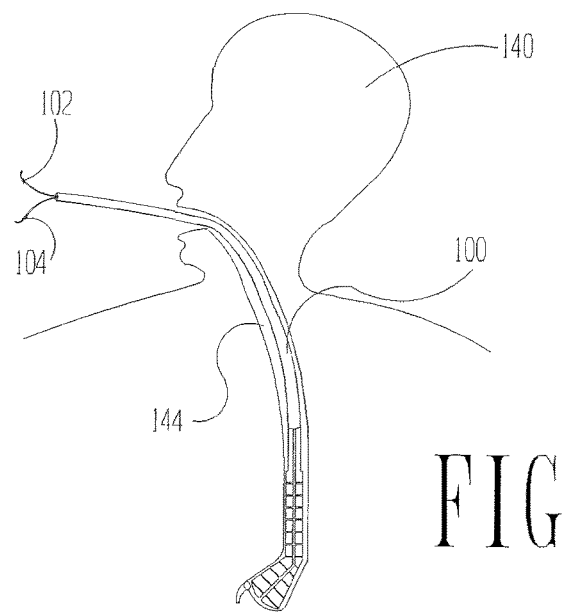
FIG. 8 depicts the deflation and removal of the device.
Figure 9:
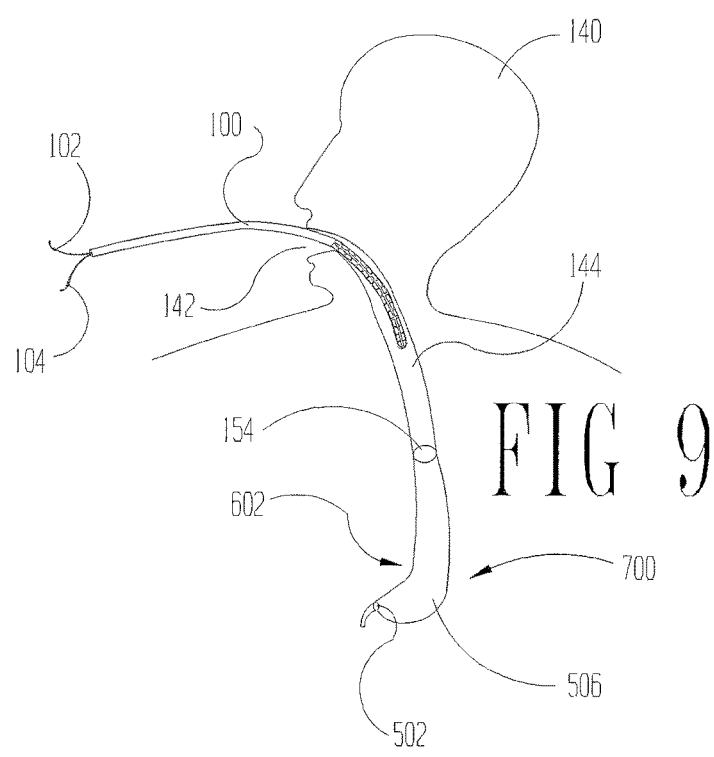
FIG. 9 shows the removal of the device through the patient's esophageal tract and mouth.

FIGS. 8 and 9 show the removal of the claimed apparatus. Once the sealing has been performed, the suction pump or negative pressure pump of the suction controlling channel 102 may be disengaged, thereby releasing the negative pressure to the plurality of hollow channel openings 108 on the outer edges of the inflated balloon 110. In a preferred embodiment, this allows the balloon to un-affix itself from the walls of the patient's stomach 150. Once the negative pressure through the suction control channel 102 and hollow channel openings 108 has been removed, in one embodiment, the inflation pump may be disengaged from the inflation controlling channel 104, thereby releasing the air or gas from the balloon 110 and out of the proximal end of the inflation controlling channel 104 outside of the patient's body. In another embodiment, the inflation pump may be capable of actively applying negative pressure to deflate the balloon 110 through the inflation controlling channel 104.

In one embodiment, once the balloon 110 has been deflated, the balloon 110 may be pulled back up through the patient's esophageal sphincter 154 by pulling the inflation controlling channel 104 and the suction controlling channel 102 attached to the insertion tube 100 and balloon 110. In another embodiment, a line may be attached to the insertion tube 100 or cylindrical outer sheath 112 to be used for retrieving the entire apparatus once the balloon 110 is deflated. In the preferred embodiment, the entire apparatus is pulled up through the patient's esophageal tract 144 and out of the patient's mouth 142, completing removal. In one embodiment, the entire apparatus may be removed once the balloon 110 is fully deflated and the inflation controlling channel 104 is capped. In another embodiment, the entire apparatus may be removed once the inflation pump is disengaged from the inflation controlling channel 104 and the gas or liquid is released, as least partially deflating the balloon 110.

What is claimed is:

1. A method of treating a patient, the method comprising the steps of:
   inserting a cylindrical sheath of gastric reduction surgery assistance apparatus through the patient's mouth and into the patient's esophageal tract;
   deploying a balloon from the cylindrical sheath into the patient's stomach, wherein the balloon includes a plurality of channel openings extending through the balloon from a converged channel within the balloon;
   inflating the balloon within the patient's stomach;
   sealing the balloon against the patient's stomach's inner walls;
   excising at least a portion of the patient's stomach; and
   removing the balloon and the cylindrical sheath of the gastric reduction surgery assistance apparatus from the patient.

2. The method of claim 1, further comprising the step of aligning the balloon with a lesser curvature of the patient's stomach before sealing the balloon against the patient's stomach's inner walls.

3. The method of claim 1, wherein the inflating step further comprises inflating the balloon into an antrum of the patient's stomach.

4. The method of claim 1, wherein the length of the balloon is 13 to 17 centimeters.

5. The method of claim 4, wherein a distal end of the balloon is angled when inflated to between 130 and 140 degrees.

6. The method of claim 5, wherein the distal end of the balloon is a distal 3 to 7 centimeters of the balloon.

7. The method of claim 6, wherein when the balloon is inflated, a proximal 8 to 12 centimeters of the balloon is between 35 and 45 French, and the distal end of the balloon is a bell shape including a proximal end and a distal end, wherein the proximal end of the bell shape is 35 to 45 French and the distal end of the bell shape is 145 to 155 French.

8. The method of claim 1, wherein sealing the balloon against the patient's stomach's inner walls includes applying a negative pressure to the converged channel and the plurality of channel openings.

9. The method of claim 1, wherein sealing the balloon against the patient's stomach's inner walls includes sealing the balloon against lesser curvature lateral, anterior, and posterior internal walls of the patient's stomach.

10. The method of claim 1, wherein in the excising step, the at least one portion comprises a portion of a greater curvature lateral stomach not sealed to the balloon.

11. The method of claim 1, further comprising sealing the patient's stomach together around the balloon after the excising step.

12. The method of claim 11, wherein sealing the patient's stomach is performed via stapling.

13. The method of claim 11, wherein sealing the patient's stomach is performed via suturing.

14. The method of claim 8, wherein the removing step comprises disengaging the negative pressure.

15. The method of claim 1, further comprising deflating the balloon before removing the cylindrical sheath of the gastric reduction surgery assistance apparatus from the patient.

16. The method of claim 1, wherein the removing step comprises removing the gastric reduction surgery assistance apparatus through the patient's esophageal tract and out through the patient's mouth.

17. A method of performing gastric reduction surgery using an assistance device, the method comprising the steps of:
   inserting the assistance device into a patient's mouth, wherein the assistance device comprises:
      a cylindrical sheath including a proximal end and a distal end; and
      a balloon member including:
         a balloon configured to be retractable into the cylindrical sheath,
         a converged channel within the balloon,
         a plurality of channel openings extending through the balloon from the converged channel,
         an inflation controlling channel for inflating the balloon, and
         a suction controlling channel for applying negative pressure to the converged channel and the plurality of channel openings, wherein the suction controlling channel is connected to the converged channel;
      wherein the balloon is configured to be deployable from the distal end of the cylindrical sheath;
   deploying the balloon into the patient's stomach;
   applying a negative pressure to the converged channel and the plurality of channel openings to seal the patient's stomach to the balloon;
   excising at least a portion of the patient's stomach;
   sealing the patient's stomach; and
   removing the assistance device.

18. The method of claim 17, wherein the assistance device further comprises a pump.

19. The method of claim 18, wherein the pump is a suction pump, an inflation pump, or both.

20. The method of claim 17, wherein a distal end of the balloon is a bell shape.

* * * * *